United States Patent
Shenderova

(10) Patent No.: US 8,728,429 B2
(45) Date of Patent: May 20, 2014

(54) PRODUCTION OF CONDUCTIVE NANODIAMOND BY DYNAMIC SYNTHESIS APPROACHES

(75) Inventor: Olga Shenderova, Raleigh, NC (US)

(73) Assignee: International Technology Center, Raleigh, NC (US)

( * ) Notice: Subject to any disclaimer, the term of this patent is extended or adjusted under 35 U.S.C. 154(b) by 665 days.

(21) Appl. No.: 12/820,230

(22) Filed: Jun. 22, 2010

(65) Prior Publication Data

US 2010/0254884 A1 Oct. 7, 2010

Related U.S. Application Data

(63) Continuation-in-part of application No. 12/660,457, filed on Feb. 26, 2010.

(60) Provisional application No. 61/156,571, filed on Mar. 2, 2009, provisional application No. 61/162,457, filed on Mar. 23, 2009, provisional application No. 61/233,950, filed on Aug. 14, 2009, provisional application No. 61/219,804, filed on Jun. 24, 2009.

(51) Int. Cl.
- *B01J 3/06* (2006.01)
- *B01J 19/08* (2006.01)
- *E21C 37/00* (2006.01)
- *B22F 3/08* (2006.01)
- *B82Y 40/00* (2011.01)
- *B82Y 5/00* (2011.01)
- *B82Y 30/00* (2011.01)
- *B82Y 15/00* (2011.01)

(52) U.S. Cl.
CPC ............... *B82Y 40/00* (2013.01); *B82Y 30/00* (2013.01); *B82Y 15/00* (2013.01); *B82Y 5/00* (2013.01); *Y10S 977/734* (2013.01); *Y10S 977/773* (2013.01); *Y10S 977/775* (2013.01); *Y10S 977/70* (2013.01)

USPC .................... 423/446; 423/445 B; 149/108.2; 299/13; 664/84; 977/734; 977/773; 977/775; 977/700

(58) Field of Classification Search
None
See application file for complete search history.

(56) References Cited

U.S. PATENT DOCUMENTS 4,483,836 A * 11/1984 Adadurov et al. ............ 423/290
4,799,963 A 1/1989 Basil et al.

(Continued)

FOREIGN PATENT DOCUMENTS

| DE | 19933648 A1 * | 1/2001 |
| KR | 2004-105096 | 12/2004 |
| WO | WO 2007/027656 | 3/2007 |

OTHER PUBLICATIONS

Machine translation of DE 19933648; Jul. 5, 2013.*

(Continued)

*Primary Examiner* — Guinever Gregorio
(74) *Attorney, Agent, or Firm* — Miller Patent Services; Jerry A. Miller

(57) ABSTRACT

In certain implementations, a method of manufacturing electrically conductive nanodiamond particles involves providing at least one type of carbon-containing explosive material and at least one type of non-explosive material; wherein the non-explosive material contains at least one or more than one element or species other than nitrogen that serve as a nano-diamond dopant; mixing the carbon containing explosive material with the non-explosive material; detonating the mixture under conditions of negative oxygen balance in the presence of a cooling medium; purifying the product of detonation from incombustible impurities; and carrying out additional processing for activation or enhancement of electrical conductance. This abstract is not to be considered limiting, since other embodiments may deviate from the features described in this abstract.

31 Claims, 1 Drawing Sheet

(56) References Cited

U.S. PATENT DOCUMENTS

| | | | |
|---|---|---|---|
| 5,861,349 A | 1/1999 | Vereschagin et al. | |
| 5,866,059 A | 2/1999 | Fujiwara et al. | |
| 6,264,859 B1 | 7/2001 | Basil et al. | |
| 6,455,442 B1 | 9/2002 | Bauer et al. | |
| 7,224,039 B1 | 5/2007 | McGuire et al. | |
| 7,534,296 B2 * | 5/2009 | Swain et al. | 117/68 |
| 7,867,467 B2 * | 1/2011 | Dolmatov | 423/446 |
| 8,070,988 B2 | 12/2011 | Shenderova et al. | |
| 8,323,609 B2 * | 12/2012 | Barker et al. | 423/447.8 |
| 8,506,920 B2 * | 8/2013 | Swanson | 423/446 |
| 2004/0016397 A1 | 1/2004 | Carlson et al. | |
| 2004/0202601 A1 | 10/2004 | Wen et al. | |
| 2005/0158549 A1 | 7/2005 | Khabashesku et al. | |
| 2008/0113448 A1 | 5/2008 | Sun | |
| 2008/0118966 A1 | 5/2008 | Chang et al. | |
| 2009/0004092 A1 * | 1/2009 | Dolmatov | 423/446 |
| 2009/0220556 A1 | 9/2009 | Shenderova et al. | |
| 2009/0285744 A1 * | 11/2009 | Sugihara et al. | 423/446 |
| 2009/0297828 A1 | 12/2009 | Shenderova et al. | |
| 2010/0028675 A1 * | 2/2010 | Gogotsi et al. | 428/402 |
| 2010/0068503 A1 | 3/2010 | Neogi et al. | |
| 2010/0190007 A1 | 7/2010 | Wu | |
| 2010/0278712 A1 * | 11/2010 | Swanson | 423/446 |
| 2010/0285304 A1 | 11/2010 | Wu | |
| 2012/0304545 A1 * | 12/2012 | Park et al. | 51/307 |
| 2013/0091763 A1 * | 4/2013 | Rottner et al. | 44/504 |
| 2013/0121909 A1 * | 5/2013 | Petrov et al. | 423/446 |
| 2014/0004031 A1 * | 1/2014 | Norwood et al. | 423/446 |

OTHER PUBLICATIONS

Beveratos, Alexios et al., "Nonclassical Radiation from Diamond Nanocrystals," Physical Review A, vol. 64, pp. 061802-1-061802-4, 2001.

Borjanovic, Vesna et al., "Effect of Proton Irradiation on Photoluminescent Properties of PDMS—Nanodiamond Composites," Nanotechnology 19, 2008.

Cabria, I. et al., "Interaction of Narrow Carbon Nanotubes with Nitronium Tetrafluoroborate Salts," The Journal of Chemical Physics 128, pp. 2147031-214703-8, 2008.

Huang, L. C. et al., "Adsorption and Immobilization of Cytochrome $c$ on Nanodiamonds," Langmuir 20, pp. 5879-5884, 2004.

Ray, S.C. et al., "Fluorescent Carbon Nanoparticles: Synthesis, Characterization and Bioimaging Application," Journal of Physical Chemistry C, 113, pp. 18546-18551, 2009.

Sun, Ya-Ping et al., "Doped Carbon Nanoparticles as a New Platform for Highly Photoluminescent Dots," The Journal of Physical Chemistry Letters 112, pp. 18295-18298, 2008.

Sun, Ya-Ping et al, "Quantum Sized Carbon Dots for Bright and Colorful Photoluminescence," Journal of American Chemical Society 128, pp. 7756-7757, 2006.

Wang, Xin et al., "Photoinduced Electron Transfers with Carbon Dots,"Chemical Communication, pp. 3774-3776, 2009.

Xu, Xiaoyou et al, "Electrophoretic Analysis and Purification of Fluorescent Single-Walled Carbon Nanotube Fragments," Journal of American Chemical Society 126, pp. 12736-12737, 2004.

Yeap, Weng Siang et al., "Using Detonation Nanodiamond for the Specific Capture of Glycoproteins," Analytical Chemistry vol. 80, No. 12, pp. 4659-4665, 2008.

Yu, Shu-Jung et al., "Bright Fluorescent Nanodiamonds: No Photobleaching and Low Cytotoxicity," Journal of American Chemical Society 127, pp. 17604-17605, 2005.

Zelezko, F. et al, "Single Defect Centres in Diamond: A Review," Phys. Stat. Sol. (a) 203, No. 13, pp. 3207-3225, 2006.

Zhang, Gaixia et al., "The Surface Analytical Characterization of Carbon Fibers Functionalized by $H_2SO_4/HNO_3$ Treatment," Science Direct, Carbon 46, pp. 196-205, 2008.

Ay et al, "The Physicochemical and Electrochemical Properties of 100 and 500 nm Diameter Diamond Powders Coated with Boron-Doped Nanocrystalline Diamond," Journal of the Electrochemical Society, 155 (10), pp. B1013-B1022, May 5, 2008.

Patel, Ronak C., USPTO Examiner, Office Action for U.S. Appl. No. 12/660,457, Jan. 29, 2013.

Patel, Ronak C., USPTO Examiner, Final Office Action for U.S. Appl. No. 12/660,457, Sep. 23, 2013.

Geis, M.W. et al., "A New Surface Electron-emission Mechanism in Diamond Cathodes," Nature, vol. 393, pp. 431-435, Jun. 4, 1998.

Shenderova, Olga A., et al., "Nitrogen Control in Nanodiamond Produced by Detonation Shock-wave-assisted Synthesis," The Journal of Physical Chemistry, pp. 14014-14024, 2011.

* cited by examiner

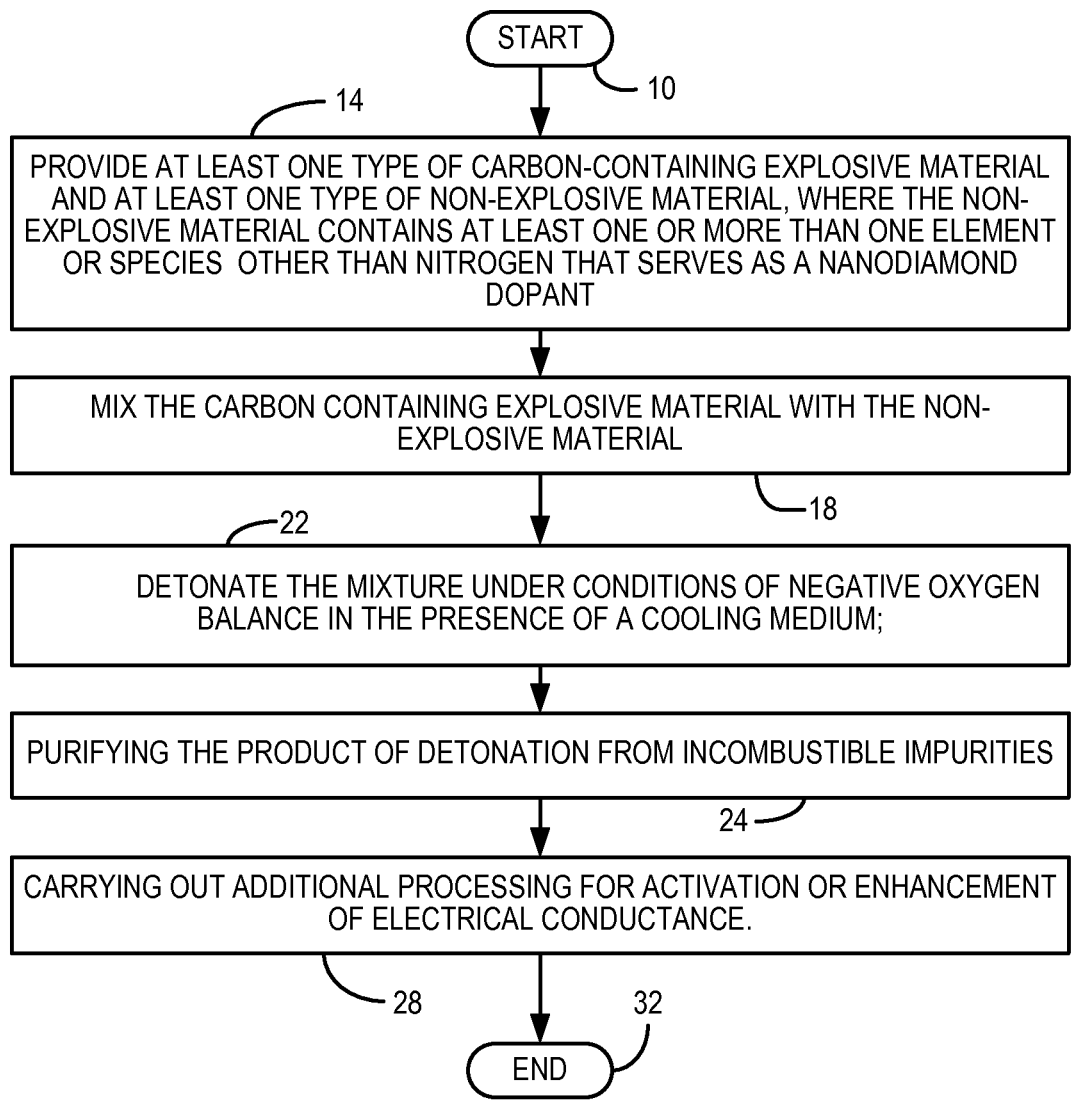

PRODUCTION OF CONDUCTIVE NANODIAMOND BY DYNAMIC SYNTHESIS APPROACHES

CROSS REFERENCE TO RELATED DOCUMENTS

This application is a continuation-in-part of U.S. patent application Ser. No. 12/660,457 filed Feb. 26, 2010 which claims priority benefit of U.S. Provisional Patent Applications No. 61/156,571, filed Mar. 2, 2009, U.S. Provisional Patent Applications No. 61/162,457 filed Mar. 23, 2009 and U.S. Provisional Patent Applications No. 61/233,950 filed Aug. 14, 2009; and which further claims priority benefit of U.S. Provisional Patent Application No. 61,219,804 filed Jun. 24, 2009 and U.S. Provisional Patent Applications No. 61/233,950 filed Aug. 14, 2009, each of which are hereby incorporated herein by reference.

STATEMENT REGARDING FEDERALLY SPONSORED RESEARCH OR DEVELOPMENT

Research relating to the technology described herein was sponsored in part by the Army Research Laboratory under Cooperative Agreement Number W911NF-04-2-0023; and in part by SPAWARSYSCEN San Diego under Grant No. N66001-04-1-8933. A portion of the research relating to the present technology was not federally sponsored.

COPYRIGHT AND TRADEMARK NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever. Trademarks are the property of their respective owners.

BACKGROUND

Synthetic undoped pure diamond in the form of films and powder is a dielectric. Diamond films grown by chemical vapor deposition (CVD) doped during synthesis with boron, for example, become conductive and find applications such as electrode material. Production of electrically conductive nanodiamond (ND) particles can be also very beneficial and can find broad applications in high surface area carbon electrode materials in electroanalysis, electrochemical double-layer capacitors, storage materials for batteries, as a possible electrocatalyst support material for fuel cells, stationary support for liquid chromatography and other applications. The electrical conductivity of nanodiamond in particulate form can be achieved, for example, by CVD growth of a film of conductive boron-doped nanodiamond surrounding a core dielectric diamond nanoparticle(s) However, this approach is costly and cannot be easily scaled up.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which FIG. 1 is a flow chart of an example process of doping a nanodiamond material during detonation in an implementation consistent with certain embodiments of the present invention.

DETAILED DESCRIPTION

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment", "an example", "an implementation" or similar terms means that a particular feature, structure, or characteristic described in connection with the embodiment, example or implementation is included in at least one embodiment, example or implementation of the present invention. Thus, the appearances of such phrases or in various places throughout this specification are not necessarily all referring to the same embodiment, example or implementation. Furthermore, the particular features, structures, or characteristics may be combined in any suitable manner in one or more embodiments, examples or implementations without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

For purposes of this document, the prefix "nano" as used, for example in "nanoparticle" is intended to refer to particles having length in at least one dimension in the range of approximately 1-100 nanometers. However, in some particular cases, the length scale for achieving the novel properties and phenomena consistent with certain embodiments of the present invention may be less than 1 nanometer or be slightly larger than 100 nanometers.

As was previously noted, synthetic undoped pure diamond in the form of films and powder is a dielectric. Diamond films grown by chemical vapor deposition (CVD) doped during synthesis with boron, for example, become conductive and find applications such as electrode material. Production of electrically conductive nanodiamond (ND) particles can be also very beneficial and can find broad applications in high surface area carbon electrode materials in electroanalysis, electrochemical double-layer capacitors, storage materials for batteries, as a possible electrocatalyst support material for fuel cells, stationary support for liquid chromatography and other applications. Boron also increases the oxidation resistance of carbon-based materials. The electrical conductivity of nanodiamond in particulate form can be achieved, for example, by CVD growth of a film of conductive boron-doped nanodiamond around a core dielectric diamond nanoparticle(s) This approach is costly and can not be easily scaled up. Production of conductive nanodiamond particles during their synthesis would be much less expensive and beneficial for many applications. Bead milling of microscopic-size boron-doped diamond particles (produced by static synthesis method, for example) can be used to produce nanoparticles.

One of the methods of production of conductive nanodiamonds is incorporation of a dopant (non-carbon element) into the diamond lattice during dynamic synthesis based upon detonation of explosives. This can be done by incorporating the dopant element into the carbon-containing explosive precursor material or mixing the doping material with the precursor material used for diamond production. These compositions become a part of the detonation charge.

Dopant material can be also added to the cooling media surrounding the detonation charge in the vessel in which the material will be detonated. Examples of the cooling medium include inert gases (nitrogen, argon, $CO_2$), water, ice, liquid nitrogen, and other coolants inert to the transformed material.

Doping elements incorporated within the precursor material composition can be in a solid, liquid or gaseous form; in the form of an atom, ion or part of a molecule or a solid state material. Precursor materials for dynamic synthesis of nanodiamond can be a mixture of carbon-containing explosives such as cyclotrimethylenetrinitramine (hexogen), cyclotetramethylenetetranitramine (octogen), trinitrotoluene (trotyl), trinitrophenylmethylnitramine (tetryl), pentaerythritol tetranitrate (PETN), tetranitromethane (TNM) or others, or mixtures of said explosives. It can also be a mixture of carbon-containing non-explosive material (graphite, hexagonal graphite, rhombohedral graphite, colloidal graphite, pyrolytic graphite, carbon black, glassy carbon, carbon soot, detonation soot, vitreous coal coke, coke, schungaite, sugar carbon, liquid hydrocarbons, e.g. octane, benzene, nitrobenzene; solid hydrocarbons, e.g. paraffin, polyethylene, polymers and others) and explosives.

Dopant elements or species can be incorporated into precursor material by different means. For example, boron-doped graphite can be used as a precursor to produce boron-doped diamond. Graphite can contain substitutional boron up to several percent (e.g. up to 2-3% by mass). There are also other carbon-based materials containing boron which can be used as the precursor material such as boron-doped fullerenes, carbon nanotubes, graphite intercalated with boron, boron-doped amorphous carbon and other carbon-based materials with the addition of boron. The content of boron in the amorphous carbon is about 15 wt %. Methods of incorporation of boron into precursor carbon material include high temperature furnace firing or low-pressure vacuum deposition. The high temperature route usually involves precursors (such as boric oxide and coke or other carbon powder) manually mixed and placed in a furnace, followed by heating to around 2900° C. An example of this method includes co-impregnation and carbonization of sucrose and boric acid. Vacuum deposition routes (chemical vapor deposition, pulsed laser deposition, and ion beam deposition) use reaction chambers and hydrocarbons and boron-containing gas ($BCl_3$, for example) mixtures and deposit thin films onto substrates in smaller quantities, but with higher boron content (up to 15 wt %). Another method of incorporating boron into graphite is the molten salt method. $H_3BO_3$-graphite intercalated compounds were prepared through the reaction of graphite with molten boric acid in vacuum (Key Engineering Materials Vols. 259-260 (2004) pp. 42-45). The boron content of graphite intercalated compounds can be controlled by adjusting the ratio of $H_3BO_3$ and graphite. The boron concentration should preferably be adjusted in the boron-doped graphite so that the amount of boron in the resulting nanodiamond product is at the level of $10^{18}$ to $10^{21}$ cm$^{-3}$. Other levels of doping are also possible. A desirable level of doping for certain applications will provide conductivity higher than approximately 0.1-1 S/cm. Such a level of doping can be readily determined experimentally.

Boron is available in soluble forms including chlorides, nitrates and acetates. These compounds are also manufactured as solutions at specified stoichiometries and can be obtained, for example, from americanelements.com. Nanoparticles of boron carbide (nano-$B_4C$), which can be also used as an additive to the precursor material, are also available from American Elements, Merelex Corporation, Los Angeles, Calif.

Similarly, other types of doping elements can be incorporated into the precursor material. When interested in doping nanodiamond with metals, nanopowder of different metal-containing components can be used. Metallic cores can be surrounded by carbon shells. Dopants can be donors or acceptors in diamond. Nitrogen, phosphorus, and sulphur are donors; arsenic, antimony and sodium (occupying an interstitial site) are promising candidates for shallow donors in diamond as well. Lithium and transition elements as well as some complexes (N—H—N, $NSi_4$) have been proposed as possible shallow donors.

The detonation charge can contain dopant-containing components in the form of finely-dispersed fractions or granules prepared at least from one component of the charge or from various combinations of such components. For mixing and dispersing of the components into fine fractions of the charge, different methods of preparation can be used such as bead milling, sonication of liquids, magnetic stirring and other methods. For example, hexogen can be dissolved in dimethyl formamide and thoroughly mixed with finely ground boron-doped graphite, then precipitated for collection through the addition of water.

As was discussed above, one of the possible approaches to dynamic synthesis of conductive nanodiamond (ND) is doping with boron. Boron should relatively easily incorporate into a substitutional site of the diamond lattice due to the negative formation energy. There are several variations of the method of dynamic synthesis based upon the choice of precursor material used to produce ND, examples of which are described below. (Method 1) The precursor material can be a non-explosive carbon-containing material converted to diamond by compression due to the shock wave created by detonation of explosives. In this method the precursor carbon material is isolated from the explosives. (Method 2) In another method ND is produced from carbon contained in the explosives themselves (so called detonation ND). (Method 3) In another method ND is produced from a mixture of carbon containing material and explosives. All of these three methods can provide ND with different primary grain sizes (average grain size being ~20 nm, ~10 nm and ~5 nm correspondingly for pure carbon, carbon/explosives mixture and pure explosives used as precursors). While for production of doped ND by methods 1 and 3 the use of carbon precursors containing boron or other doping elements can be beneficial; for method 2 a mixture of explosives with substances containing boron (for example boric acid), is another way to proceed. One of the barriers for producing conductive detonation ND by doping with boron from a mixture of explosives, for example TNT/RDX, is the high nitrogen content in the explosive mixture and the resultant high nitrogen content in the detonation ND. Nitrogen is a donor in diamond and compensates the contribution of the acceptor, for example boron, to the electrical conductivity. The nitrogen content incorporated into the core of the detonation ND particles produced from TNT/RDX is approximately 10,000-20,000 ppm; this is distinct from nitrogen that may be attached to the particle surface in the form of functional groups, for example, that do not influence the particles inherent electrical properties. The high N content in ND originates from the high N content in the precursor explosives themselves (TNT (trinitrotoluene), RDX(hexane) and others) used for detonation ND (DND) synthesis. For example, in a 50/50 mixture of TNT/RDX there is approximately 21 at. % of N. Thus, the level of nitrogen in the starting material should be controlled by different means. The addition of graphite (or other carbon material that does not contain N) to the precursor used for detonation synthesis, allows one to reduce the overall N content in the precursor, thus resulting in reduced N content in the produced ND. The N content in ND produced by the high pressure-high temperature (HPHT) method can be up to about 300 ppm. It is also possible to synthesize ND using a combination of explosives with lower N content than in the TNT/RDX mixture. For example, hexanitrostilbene (HNS, C14H6N6O12) contains less N per C atom. In the 50/50 mixture of TNT and HNS, there is approximately ~15 at % of N (less than in the TNT/RDX mixture). Thus, a variation in the type of explosive used as the precursor also provides some variation in N content in the final ND product, however, the N content is still too high to achieve the desired N content to produce conductive ND. The various explosives can be used together with the addition of other carbon precursor materials that contain low or little N as starting material to reduce the overall N content. In applications where the goal is to produce conductive ND, the aim is to produce ND material with a substitutional N content lower than approximately 1,000 ppm and most preferably lower than 100 ppm.

Other methods of diamond doping besides in-situ incorporation or kinetic trapping during growth are in-diffusion and ion implantation. In-diffusion can be performed, in principle, under pressure from a gas (for example $B_2H_6$) or a liquid ($H_3BO_3$, solutions of boron-containing salts, and other compounds) containing boron.

It is also preferable to assure that other bulk or surface structural defects and groups are not electrically active and do not compensate the electrical activity of boron. Boron reduces the density of planar defects in CVD diamond. This property in principle can extend to nanodiamond particles doped with boron.

Inert additives such as water, ice, liquid nitrogen, aqueous solutions of salts of metals, and crystal hydrates can be used as additives incorporated into the detonation charge (see U.S. Pat. No. 4,483,836, which is hereby incorporated by reference). Such additives, are used as so called cooling media, decompose or evaporate with an accompanying absorption of heat to reduce the temperature of detonation products, and thus help to preserve the desired product, ND, in the detonation products. The purpose of adding doping elements into the charge so that it is incorporated into the resulting diamond lattice in our approach is different. It is aimed at changing the fundamental electrical properties of ND, namely the electrical conductivity.

It is also possible to use laser irradiation for phase conversion of the carbon (non-diamond) precursor to produce ND with controlled dopant content. Laser irradiation of onion-like carbon (OLC) as the precursor with a controlled amount of intercalated dopant may also produce doped ND. In the literature, pulsed laser irradiation of the precursor micrographite dispersed in a liquid was reported as a means to produce nanodiamond. Here we propose the use of doped OLC to better control the resulting ND size and, in addition, the dopant content. Doping of OLC can be done as described above for graphite and other carbon-based materials. Boron-doped graphite or other carbon material can be also used for this purpose.

ND terminated with hydrogen with low nitrogen content can also possess enhanced surface conductivity and can be also used in applications requiring electrically conductive NDs. Conductivity acquired due to the presence of a surface $sp^2$ phase is not desirable, since a $sp^2$ phase can more easily chemically react than $sp^a$ carbon during applications in a harsh environment. However, if conductivity is achieved due to grain boundary conductivity (due to doping and $sp^2$ C phase) and these grain boundaries are well isolated from the harsh chemical environment (as in very tight agglomerates/polycrystals), conductivity through grain boundaries can also contribute to the total conductivity.

With reference to FIG. 1, a method of manufacturing electrically conductive nanodiamond particles starts at 10 and involves providing at least one type of carbon-containing explosive material and at least one type of non-explosive material; wherein the non-explosive material contains at least one or more than one element or species other than nitrogen that serve as a nanodiamond dopant. At 18, the carbon containing explosive material is mixed with the non-explosive material. The mixture is detonated at 22 under conditions of negative oxygen balance in the presence of a cooling medium. At 26 the product of detonation is purified from incombustible impurities. At 28 additional processing can be carried out for activation or enhancement of electrical conductance. The process ends at 32.

Thus, it is submitted that detonation of a mixture of at least one type of high energy explosive precursor material wherein the dopant element is incorporated into the carbon-containing explosive or a high energy carbon-based explosive mixed with a doped carbon precursor such as, for example, graphite, carbon black, carbon fibers, hydrocarbons and other carbon-containing precursors for production of conductive ND. ND synthesized by the above means can have low nitrogen content in an amount that will not fully compensate the conductivity of boron or other p-type dopants. Precursor graphite can be also intercalated with different elements. Since graphite as a precursor contains very little N, only as a trace impurity, it allows one to generate ND with a low N content. Elements intercalated into graphite can be also incorporated into the core ND structure. There can be a mixture of carbon-containing precursor materials and dopant-containing substances. The dopant can be also added to the cooling media.

Boron-doped ND can be also produced by Method 1 as described above. The precursor material can be a non-explosive carbon-containing material enriched with boron which is converted to diamond by compression due to the shock wave created by detonation of explosives located externally to the carbon precursor. In this method the precursor carbon material is isolated from the explosives and can be mixed with metal powder.

A process for production of nanodiamond by the method of dynamic synthesis (using explosives), a method of manufacturing of electrically conductive nanodiamond particles, should further include: providing at least one type of carbon-containing explosive material and at least one type of non-explosive material; wherein the non-explosive material serves as a source of dopants other than nitrogen for the nanodiamond-containing material that is produced by dynamic synthesis; mixing the carbon containing explosive material with the non-explosive material; detonating the mixture under conditions with negative oxygen balance in the presence of a cooling medium; purifying the product of detonation from incombustible impurities; and carrying out purification of the product of detonation from non-diamond carbon impurities; and processing for activation or enhancement of electrical conductance. For example, annealing of the produced and purified doped nanodiamond material can further enhance electrical conductivity due to lattice relaxation of the dopants.

Thus, in certain implementations, a method of manufacturing electrically conductive nanodiamond particles involves providing at least one type of carbon-containing explosive material and at least one type of non-explosive material; wherein the non-explosive material contains at least one or more than one element or species other than nitrogen that serve as a nanodiamond dopant; mixing the carbon containing explosive material with the non-explosive material; detonating the mixture under conditions of negative oxygen balance in the presence of a cooling medium; purifying the product of detonation from incombustible impurities; and carrying out additional processing for activation or enhancement of electrical conductance.

In certain implementations, the additional processing includes purifying the product of detonation from non-diamond carbon impurities. In certain implementations, the additional processing includes annealing. In certain implementations, at least a portion of the explosive material is selected from the group consisting of: trinitrotoluene, hexogen, hexanitrostilbene, benzotrioxofuraxan, triamino-trinitrobenzene, or other carbon-containing explosives; and where a combination of explosives is chosen in order to minimize the nitrogen content of the starting explosive material so that the nitrogen available to be incorporated into the lattice of nanodiamond particles produced is limited. In certain implementations, at least a portion of the non-explosive material is selected from the group consisting of: non-diamond carbon, graphite, hexagonal graphite, rhombohedral graphite, colloidal graphite, pyrolytic graphite, soot, carbon black, hydrocarbons, polyaromatic hydrocarbons, glassy carbon, carbon soot, detonation soot, vitreous coal coke, coke, schungaite, sugar carbon, liquid hydrocarbons, (octane, benzene, nitrobenzene); solid hydrocarbons (paraffin, polyethylene, polymers), doped non-diamond carbon, doped graphite, doped soot, doped carbon black, intercalated non-diamond carbon, intercalated graphite, intercalated soot, intercalated carbon black, boron-containing compounds, boric acid, boron salts, boron carbide, boron-doped fullerenes, boron-doped carbon nanotubes, boron-doped graphite, $H_3BO_3$-graphite intercalated compounds, graphite intercalated with boron, boron-doped amorphous carbon, metal-containing compounds, and wherein at least one dopant atom or intercalated element atom is incorporated into the diamond lattice. In certain implementations, elements for doping and/or intercalation of the non-explosive material are selected from the group consisting of: boron, phosphorus, sulphur, arsenic, antimony, sodium, lithium and transition metal elements.

In certain implementations, the cooling media contains boron atom containing compounds comprising a gas (for example $B_2H_6$) or a liquid ($H_3BO_3$, solutions of boron-containing salts), or other compounds.

In certain implementations, explosive material contains at least one or more than one element or species other than nitrogen that serve as a nanodiamond dopant. In certain implementations, boron-containing explosive materials (for example borazines, azidoborazines or other explosives) mixed with carbon-containing explosives and/or non-explosive carbon precursor serve as a nanodiamond dopant.

In certain implementations, a nanodiamond-containing material with enhanced electrical conductivity can be produced according to any of the methods described herein.

In certain implementations, a method of manufacturing electrically conductive nanodiamond particles, involves providing at least one type of carbon-containing explosive material and at least one type of non-explosive material; where at least a portion of the explosive material is selected from the group consisting of: trinitrotoluene, hexogen, hexanitrostilbene, benzotrioxofuraxan, triamino-trinitrobenzene, or other carbon-containing explosives; wherein the non-explosive material contains at least one or more than one element or species other than nitrogen that serve as a nanodiamond dopant selected from the group consisting of: boron, phosphorus, sulphur, arsenic, antimony, sodium, lithium and transition metal elements; mixing the carbon containing explosive material with the non-explosive material; detonating the mixture under conditions of negative oxygen balance in the presence of a cooling medium; purifying the product of detonation from incombustible impurities and from non-diamond carbon impurities; and annealing the purified product to enhance electrical conductivity.

In certain implementations, a nanodiamond-containing material produced by dynamic synthesis containing boron atom(s) in the nanodiamond particle core so that the amount of boron in the resulting nanodiamond product is at a level of approximately $10^{18}$ to $10^{21}$ cm$^{-3}$.

In certain implementations, a ND material with a substitutional N content at an amount that does not compensate the electrical activity of boron.

In certain implementations, the ND material with a substitutional N content at an amount that does not compensate the electrical activity of phosphorus, sulphur, arsenic, antimony, sodium, lithium or transition metal elements. In certain implementations, the ND material with substitutional N content at an amount lower than approximately 1,000 ppm and most preferably lower than 100 ppm. In certain implementations, the nanodiamond-containing material produced by dynamic synthesis containing phosphorus, sulphur, arsenic, antimony, sodium, lithium or transition metal elements atom(s) in the nanodiamond particle core according to claim 12 further comprising ND material with substitutional N content at an amount lower than approximately 1,000 ppm and most preferably lower than 100 ppm.

Another nanodiamond-containing material produced by dynamic synthesis contains dopant atom(s) from the group consisting of phosphorus, sulphur, arsenic, antimony, sodium (in an interstitial site), lithium and transition metal elements in the nanodiamond particle core so that the amount of dopant in the resulting nanodiamond product is at a level of approximately $10^{18}$ to $10^{21}$ cm$^{-3}$.

Another example nanodiamond-containing material containing boron atom(s) in the nanodiamond particle core is obtained by in-diffusion of boron atoms under pressure from a gas (for example $B_2H_6$) or a liquid ($H_3BO_3$, solutions of boron-containing salts, and other compounds) containing boron.

Another example nanodiamond-containing material produced by dynamic synthesis containing boron atom(s) in the nanodiamond particle core is produced by phase transformation of boron-doped graphite, graphite intercalated with boron, boron-doped amorphous carbon, boron-doped carbon black, boron-doped non-diamond carbon induced by a shock wave.

Another example nanodiamond-containing material produced by dynamic synthesis containing dopant atom(s) in the nanodiamond particle core is produced by a phase transformation of doped graphite, graphite intercalated with dopant atoms, doped amorphous carbon, doped carbon black, doped non-diamond carbon induced by a shock wave, where dopants are from the list phosphorus, sulphur, arsenic, antimony, sodium, lithium and transition metal elements.

While certain illustrative embodiments have been described, it is evident that many alternatives, modifications, permutations and variations will become apparent to those skilled in the art in light of the foregoing description.

What is claimed is:

1. A method of manufacturing electrically conductive nanodiamond material, comprising in any operative order:
   providing at least one type of explosive material and at least one type of carbon-containing non-explosive material;
   where the carbon-containing non-explosive material incorporates at least one element or species other than nitrogen, where the element or species other than nitrogen serves as a nanodiamond acceptor dopant providing electrical conductance in diamond;
   where the available nitrogen in the explosive material and the carbon-containing non-explosive material is limited to a level that prevents compensation of the electrical activity of the nanodiamond acceptor dopant in the conductive nanodiamond material;
   mixing the explosive material with the carbon-containing non-explosive material;
   detonating the mixture under conditions of negative oxygen balance in the presence of a cooling medium;
   purifying the product of detonation from incombustible impurities; and
   carrying out additional processing for activation or enhancement of electrical conductance.

2. The method of manufacturing electrically conductive nanodiamond material according to claim 1, where the additional processing includes purifying the product of detonation from non-diamond carbon impurities.

3. The method of manufacturing electrically conductive nanodiamond material according to claim 1, where the additional processing includes annealing.

4. The method of manufacturing electrically conductive nanodiamond material according to claim 1, where at least a portion of the explosive material is selected from the group consisting of: trinitrotoluene, hexogen, hexanitrostilbene, benzotrioxofuraxan, triamino-trinitrobenzene, or other carbon-containing explosives; borazines, azidoborazines or other boron-containing explosives; and where a combination of explosives is used.

5. The method of manufacturing electrically conductive nanodiamond material according to claim 1, where at least a portion of the carbon-containing non-explosive material with incorporated element or species is selected from the group consisting of: doped non-diamond carbon, doped graphite, doped soot, doped carbon black, intercalated non-diamond carbon, intercalated graphite, intercalated soot, intercalated carbon black, boron-containing carbon compounds, boron carbide, boron-doped fullerenes, boron-doped carbon nanotubes, boron-doped graphite, $H_3BO_3$-graphite intercalated compounds, graphite intercalated with boron, boron-doped amorphous carbon, metal-containing carbon compounds, and where at least one atom or element from the carbon-containing non-explosive material with incorporated element or species is incorporated into the diamond lattice.

6. The method of manufacturing of electrically conductive nanodiamond material according to claim 5, where the incorporated element or species of the carbon-containing non-explosive material are selected from the group consisting of: boron, phosphorus, sulphur, arsenic, antimony, sodium, lithium and transition metal elements.

7. The method of manufacturing electrically conductive nanodiamond material particles according to claim 5, where the method of incorporation of boron into precursor carbon material to produce boron-doped carbon precursor further comprises at least one of high temperature furnace firing, low-pressure vacuum deposition and molten salt method.

8. The method of manufacturing electrically conductive nanodiamond material according to claim 1, where boron-containing substance is added to the cooling medium and where the cooling medium surrounds the detonation charge.

9. A method of manufacturing electrically conductive nanodiamond material, comprising in any operative order:
   providing at least one type of explosive material and at least one type of carbon-containing non-explosive material;
   where the carbon-containing non-explosive material incorporates at least one element or species other than nitrogen, where the element or species other than nitrogen serves as a nanodiamond dopant providing electrical conductance in diamond;
   mixing the explosive material with the carbon-containing non-explosive material;
   detonating the mixture under conditions of negative oxygen balance in the presence of a cooling medium surrounding the detonation charge;
   purifying the product of detonation from incombustible impurities;
   carrying out additional processing for activation or enhancement of electrical conductance; and
   where a boron-containing substance is added to the cooling medium.

10. A method of manufacturing electrically conductive nanodiamond material, comprising in any operative order:
    providing at least one type of explosive material and at least one type of carbon-containing non-explosive material;
    where the explosive material contains at least one element or species other than nitrogen that is incorporated into the explosive material, where the element or species serves as a nanodiamond acceptor dopant providing electrical conductance in diamond;
    where the available nitrogen in the explosive material and the carbon-containing non-explosive material is limited to a level that prevents compensation of the electrical activity of the nanodiamond acceptor dopant in the conductive nanodiamond material;
    mixing the explosive material with the carbon-containing non-explosive material;
    detonating the mixture under conditions of negative oxygen balance in the presence of a cooling medium;
    purifying the product of detonation from incombustible impurities; and
    carrying out additional processing for activation or enhancement of electrical conductance.

11. The method of manufacturing electrically conductive nanodiamond material according to claim 10, where the additional processing includes purifying the product of detonation from non-diamond carbon impurities.

12. The method of manufacturing electrically conductive nanodiamond material according to claim 10, where the additional processing includes annealing.

13. The method of manufacturing electrically conductive nanodiamond material according to claim 10, where at least a portion of the explosive material is selected from the group consisting of: trinitrotoluene, hexogen, hexanitrostilbene, benzotrioxofuraxan, triamino-trinitrobenzene, or other carbon-containing explosives; borazines, azidoborazines or other boron-containing explosives and where a combination of explosives is used.

14. The method of manufacturing electrically conductive nanodiamond material according to claim 10, where at least a portion of the carbon-containing non-explosive material is selected from the group consisting of: non-diamond carbon, graphite, hexagonal graphite, rhombohedral graphite, colloidal graphite, pyrolytic graphite, soot, carbon black, hydrocarbons, polyaromatic hydrocarbons, glassy carbon, carbon soot, detonation soot, vitreous coal coke, coke, schungaite, sugar carbon, liquid hydrocarbons, solid hydrocarbons, doped non-diamond carbon, doped graphite, doped soot, doped carbon black, intercalated non-diamond carbon, intercalated graphite, intercalated soot, intercalated carbon black, boron-containing carbon compounds, boron carbide, boron-doped fullerenes, boron-doped carbon nanotubes, boron-doped graphite, $H_3BO_3$-graphite intercalated compounds, graphite intercalated with boron, boron-doped amorphous carbon, metal-containing carbon compounds, metallic cores surrounded by carbon shells, and where at least one of the element or species incorporated into the carbon-containing non-explosive material is incorporated into the diamond lattice as a nanodiamond dopant.

15. The method of manufacturing electrically conductive nanodiamond material according to claim 10, where boron-containing substance is added to the cooling medium and where the cooling medium surrounds the detonation charge.

16. A method of manufacturing electrically conductive nanodiamond material, comprising in any operative order:
providing at least one type of explosive material and at least one type of non-explosive material;
where the explosive material comprises an explosive or a combination of explosives;
where the non-explosive material contains boron in the form of an atom, ion or a boron-containing molecule or substance that serves as a nanodiamond acceptor dopant providing electrical conductance in diamond;
where the available nitrogen in the explosive material and the non-explosive material is limited to a level that prevents compensation of the electrical activity of the nanodiamond acceptor dopant in the conductive nanodiamond material;
mixing the explosive material with the non-explosive material;
detonating the mixture under conditions of negative oxygen balance in the presence of a cooling medium;
purifying the product of detonation from incombustible impurities and from non-diamond carbon impurities; and
annealing the purified product to enhance electrical conductivity.

17. The method of manufacturing electrically conductive nanodiamond material according to claim 16, where the additional processing includes purifying the product of detonation from non-diamond carbon impurities.

18. The method of manufacturing electrically conductive nanodiamond material according to claim 16, where the additional processing includes annealing.

19. The method of manufacturing electrically conductive nanodiamond material according to claim 16, where boron-containing substance is added to the cooling media and where the cooling medium surrounds the detonation charge.

20. The method of manufacturing electrically conductive nanodiamond material according to claim 16, where at least a portion of the non-explosive material is selected from the group consisting of: non-diamond carbon, graphite, hexagonal graphite, rhombohedral graphite, colloidal graphite, pyrolytic graphite, soot, carbon black, hydrocarbons, polyaromatic hydrocarbons, glassy carbon, carbon soot, detonation soot, vitreous coal coke, coke, schungaite, sugar carbon, liquid hydrocarbons, solid hydrocarbons doped non-diamond carbon, doped graphite, doped soot, doped carbon black, intercalated non-diamond carbon, intercalated graphite, intercalated soot, intercalated carbon black, boron-containing compounds, boric acid, boron salts, boron carbide, boron-doped fullerenes, boron-doped carbon nanotubes, boron-doped graphite, $H_3BO_3$-graphite intercalated compounds, graphite intercalated with boron, boron-doped amorphous carbon, metal-containing compounds, and where at least one the element or species incorporated into the carbon-containing non-explosive material is incorporated into the diamond lattice as a nanodiamond dopant.

21. A method of manufacturing electrically conductive nanodiamond material, comprising in any operative order:
providing at least one type of explosive material and at least one type of carbon-containing non-explosive material;
where the explosive material contains at least one element or species other than nitrogen that is incorporated into the explosive material, where the element or species serves as a nanodiamond dopant providing electrical conductance in diamond;
mixing the explosive material with the carbon-containing non-explosive material;
detonating the mixture under conditions of negative oxygen balance in the presence of a cooling medium surrounding the detonation charge;
purifying the product of detonation from incombustible impurities;
carrying out additional processing for activation or enhancement of electrical conductance; and
where boron-containing substance is added to the cooling medium.

22. A method of manufacturing electrically conductive nanodiamond material, comprising in any operative order:
providing at least one type of explosive material and at least one type of non-explosive material;
where the explosive material comprises an explosive or a combination of explosives selected in order to minimize nitrogen content of the explosive material so that the nitrogen available to be incorporated into a lattice of nanodiamond particles produced is limited;
where the non-explosive material contains boron in the form of an atom, ion or a boron-containing molecule or substance that serves as a nanodiamond dopant providing electrical conductance in diamond;
where the boron-containing molecule or substance is selected so that the nitrogen available to be incorporated into a lattice of nanodiamond particles produced is limited;
mixing the explosive material with the non-explosive material;
detonating the mixture under conditions of negative oxygen balance in the presence of a cooling medium surrounding the detonation charge;
purifying the product of detonation from incombustible impurities and from non-diamond carbon impurities;
annealing the purified product to enhance electrical conductivity; and
where boron-containing substance is added to the cooling medium.

23. A method of manufacturing electrically conductive nanodiamond material, comprising in any operative order:

providing at least one type of carbon-containing explosive material;

where the explosive material contains boron that serves as a nanodiamond dopant providing electrical conductance in diamond;

where the explosive material comprises an explosive or a combination of explosives selected to limit the available nitrogen in the explosive material to a level that prevents compensation of the electrical activity of the boron nanodiamond dopant in the conductive nanodiamond material;

detonating the explosive material under conditions of negative oxygen balance in the presence of a cooling medium;

purifying the product of detonation from incombustible impurities; and carrying out additional processing for activation or enhancement of electrical conductance.

24. A method of manufacturing electrically conductive nanodiamond material containing boron in a nanodiamond particle, providing a precursor non-explosive carbon-containing material containing boron-containing substance;

producing phase transformation of the precursor non-explosive carbon-containing material containing boron-containing substance;

where the phase transformation is induced by a shock wave; and where the shock wave is created by detonation of explosives and with the explosives placed externally to the precursor carbon-containing material in a manner that isolates the precursor carbon-containing material from the explosives and any nitrogen present in the explosives in order to inhibit nitrogen incorporation into the nanodiamond particle and compensation of electrical activity of the boron in the nanodiamond particle by nitrogen.

25. The method of manufacturing electrically conductive nanodiamond-containing material according to claim 24, where the precursor non-explosive carbon-containing material containing boron-containing substance is selected from the group consisting of: non-diamond carbon, graphite, hexagonal graphite, rhombohedral graphite, colloidal graphite, pyrolytic graphite, soot, carbon black, hydrocarbons, polyaromatic hydrocarbons, glassy carbon, carbon soot, detonation soot, vitreous coal coke, coke, schungaite, sugar carbon, liquid hydrocarbons, solid hydrocarbons, boric acid, boron salts, boron carbide, boron-doped fullerenes, boron-doped carbon nanotubes, boron-doped graphite, $H_3BO_3$-graphite intercalated compounds, graphite intercalated with boron, boron-doped amorphous carbon, and where at least one boron atom is incorporated into the diamond lattice.

26. The method of manufacturing electrically conductive nanodiamond-containing material according to claim 24, where the precursor non-explosive carbon-containing material containing boron-containing substance is further mixed with metal.

27. A method of manufacturing electrically conductive nanodiamond material, comprising in any operative order:

providing at least one type of explosive material and at least one type of carbon-containing non-explosive material;

where the carbon-containing non-explosive material incorporates at least one element or species other than nitrogen, where the element or species other than nitrogen serves as a nanodiamond dopant providing electrical conductance in diamond;

mixing the explosive material with the carbon-containing non-explosive material;

detonating the mixture under conditions of negative oxygen balance in the presence of a cooling medium to produce nanodiamond material, and where the available nitrogen in the explosive material and the carbon-containing non-explosive material is limited so as to result in a level of less than about 1000 ppm of nitrogen in the nanodiamond material;

purifying the product of detonation from incombustible impurities; and carrying out additional processing for activation or enhancement of electrical conductance.

28. The method of manufacturing electrically conductive nanodiamond material according to claim 27, where the available nitrogen in the explosive material and the carbon-containing non-explosive material is limited so as to result in a level of less than about 300 ppm of nitrogen in the nanodiamond material.

29. The method of manufacturing electrically conductive nanodiamond material according to claim 28, where the available nitrogen in the explosive material and the carbon-containing non-explosive material is limited so as to result in a level of less than about 100 ppm of nitrogen in the nanodiamond material.

30. The method of manufacturing electrically conductive nanodiamond material according to claim 27, where the dopant comprises a shallow dopant.

31. A method of manufacturing electrically conductive nanodiamond material, comprising in any operative order:

providing at least one type of explosive material and at least one type of carbon-containing non-explosive material;

mixing the explosive material with the carbon-containing non-explosive material;

detonating the mixture under conditions of negative oxygen balance in the presence of a cooling medium surrounding the detonation charge;

where the cooling medium contains a nanodiamond acceptor dopant;

where the available nitrogen in the explosive material and the carbon-containing non-explosive material is limited to a level that prevents compensation of the electrical activity of the nanodiamond acceptor dopant in the conductive nanodiamond material;

purifying the product of detonation from incombustible impurities; and carrying out additional processing for activation or enhancement of electrical conductance.

* * * * *